(12) United States Patent  (10) Patent No.: US 8,997,573 B2
Wright  (45) Date of Patent: Apr. 7, 2015

(54) INTERNAL STRINGER INSPECTION SYSTEM FOR INTEGRATED STRUCTURES

(75) Inventor: Allison Jean Wright, Wichita, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 68 days.

(21) Appl. No.: 13/600,395

(22) Filed: Aug. 31, 2012

(65) Prior Publication Data

US 2013/0291641 A1    Nov. 7, 2013

Related U.S. Application Data

(60) Provisional application No. 61/640,829, filed on May 1, 2012.

(51) Int. Cl.
*G01N 29/265*  (2006.01)

(52) U.S. Cl.
CPC ...... *G01N 29/265* (2013.01); *G01N 2291/2638* (2013.01)

(58) Field of Classification Search
CPC ... G01N 29/04; G01N 29/225; G01N 29/227; G01N 29/24; G01N 29/265; G01N 2294/0234; G01N 2294/0235; G01N 2294/2636; G01N 2294/2638; G01N 2294/2694; G01N 29/26; G01N 21/90

USPC ............ 73/40.5 R, 49.1, 623, 633, 641, 649, 73/865.8, 866.5, 627, 634; 376/249, 252; 356/240.1–241.6, 246.1

See application file for complete search history.

(56) References Cited

U.S. PATENT DOCUMENTS

| 2,723,357 | A | * | 11/1955 | Van Valkenburg et al. ... 310/336 |
| 3,786,684 | A | * | 1/1974 | Wiers et al. .................. 73/866.5 |
| 4,453,410 | A | * | 6/1984 | Schmitz et al. ................. 73/640 |
| 5,267,481 | A | * | 12/1993 | Smith ............................. 73/623 |
| 5,533,224 | A | * | 7/1996 | Knapp ..................... 15/104.061 |
| 6,067,846 | A | * | 5/2000 | Hill et al. ........................... 73/82 |
| 6,959,603 | B2 | * | 11/2005 | Knight et al. .................. 73/623 |

\* cited by examiner

*Primary Examiner* — Laura Martin
*Assistant Examiner* — Irving A Campbell
(74) *Attorney, Agent, or Firm* — Hovey Williams LLP

(57) ABSTRACT

An inspection apparatus and method for inspecting an interior surface of a hollow composite part. The inspection apparatus may have a first plug, a second plug, and a trolley positioned between the first and second plugs. The first and second plugs may form a leak-proof seal against the interior surface of the hollow composite part. The trolley may support at least one inspection probe for testing the interior surface of the composite part. A method of inspecting the composite part may include the steps of inserting the inspection apparatus into the hollow composite part, pushing or pulling the inspection apparatus with an elongated actuation element to a desired area to be inspected within the composite part, then filling a space between first and second plugs with a liquid. Finally, the method may include a step of inspecting the interior surface of the hollow composite part with the inspection probe.

26 Claims, 6 Drawing Sheets

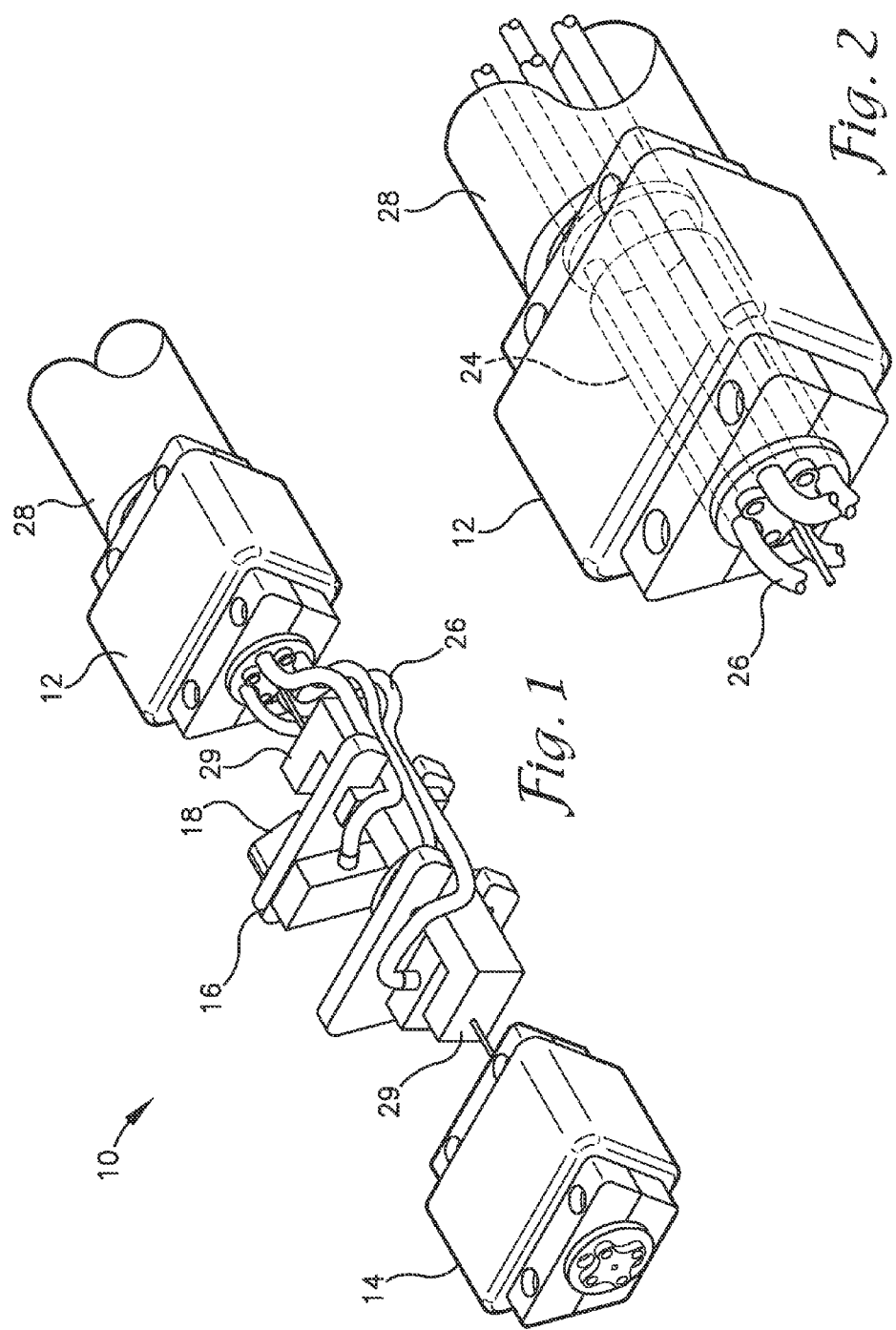

INTERNAL STRINGER INSPECTION SYSTEM FOR INTEGRATED STRUCTURES

RELATED APPLICATIONS

The present application is a non-provisional utility application claiming priority benefit to U.S. Application No. 61/640,829 entitled Internal Stringer Inspection System for Integrated Structures, filed May 1, 2012 and incorporated by reference herein in its entirety.

BACKGROUND

Composite materials are increasingly replacing metals in aerospace structural applications due to their high strength and low weight. Composite materials may also be co-cured into large, complex, integrated structures, potentially reducing weight, manufacturing costs, and fastener counts. However, these complex integrated structures are often difficult to adequately inspect because critical inspection locations are closed-in and inaccessible to existing non-destructive inspection (NDI) equipment available in the industry.

This problem commonly occurs when hollow "hat"-type stringers run through the interior of a structure and are therefore not accessible for inspection by conventional means. Inspecting aircraft stringer-rib bond lines is particularly difficult using known methods.

One known method for inspecting tubular structures, such as water pipelines, includes the use of pipeline inspection "pigs" configured to inspect inaccessible tubular structures from the inside. These pigs operate in a liquid-filled environment and are moved via fluid flowing within a pipeline with no independent means of positioning. These pipeline pigs are designed to operate in completely filled pipelines and do not provide a way of limiting immersion fluids to a specific area under inspection. Various other known methods for inspecting stringers at least partially from the inside are generally not suitable for immersion inspection techniques, such as the immersion inspection methods with pipeline pigs.

Accordingly, there is a need for an improved method of inspecting composite parts that overcomes the limitations of the prior art.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

Embodiments of the present invention solve the above-mentioned problems and provide a distinct advance in the art of composite part inspection. An inspection apparatus constructed in accordance with embodiments of the invention for inspecting a composite part may include a first plug, a second plug, and a trolley positioned between the first plug and the second plug. The first and second plugs may be sized and configured for fitting within a hollow composite part and forming a leak-proof seal against an interior surface of the hollow composite part. The second plug may be spaced a distance apart from the first plug. The trolley may be fixed or moveable relative to the first and second plugs and configured to support at least one inspection probe for testing an interior of a composite part.

In another embodiment of the invention, the inspection apparatus may include a first plug, a second plug, a trolley positioned between the first plug and the second plug, and an elongated actuation element extending through at least one of the first plug, the second plug, and the trolley. The first and second plugs may be sized and configured for fitting within a hollow composite part and forming a leak-proof seal against an interior surface of the hollow composite part. The second plug may be spaced a distance apart from the first plug. The trolley may be fixed or moveable relative to the first and second plugs and configured to support at least one inspection probe for testing an interior of a composite part. The elongated actuation element may be fixed relative to the trolley and fixed to or slidable through at least one of the first and second plugs. Furthermore, the elongated actuation element may be configured to pull or push at least one of the trolley and the first and second plugs within the composite part.

In accordance with another embodiment of the present invention, a method of inspecting an interior surface of a hollow composite part having at least one opening through which an inspection apparatus can be inserted may include the steps of inserting the inspection apparatus through the opening of the hollow composite part and pushing or pulling an elongated actuation element attached to the inspection apparatus, thus moving the inspection apparatus to a desired area to be inspected within the composite part. The inspection apparatus may include a first plug, a second plug, a trolley positioned between the first plug and the second plug, and at least one inspection probe configured for testing the interior surface of the composite part. The first and second plugs may be sized and configured for fitting within a hollow composite part and forming a leak-proof seal against an interior surface of the hollow composite part. The second plug may be spaced a distance apart from the first plug. The trolley may be fixed or moveable relative to the first and second plugs and may support the at least one inspection probe. The method may further include the steps of filling a space between the first and second plugs with a liquid, such that liquid is trapped between the first and second plugs and surrounds the trolley and the at least one inspection probe and inspecting the interior surface of the hollow composite part with the inspection probe.

BRIEF DESCRIPTION OF THE DRAWING FIGURES

Embodiments of the present invention are described in detail below with reference to the attached drawing figures, wherein:

FIG. 1 is a perspective view of an inspection apparatus constructed in accordance with an embodiment of the invention;

FIG. 2 is a perspective view of one plug of the inspection apparatus of FIG. 1 illustrating data cables extending therethrough;

Figure 3:
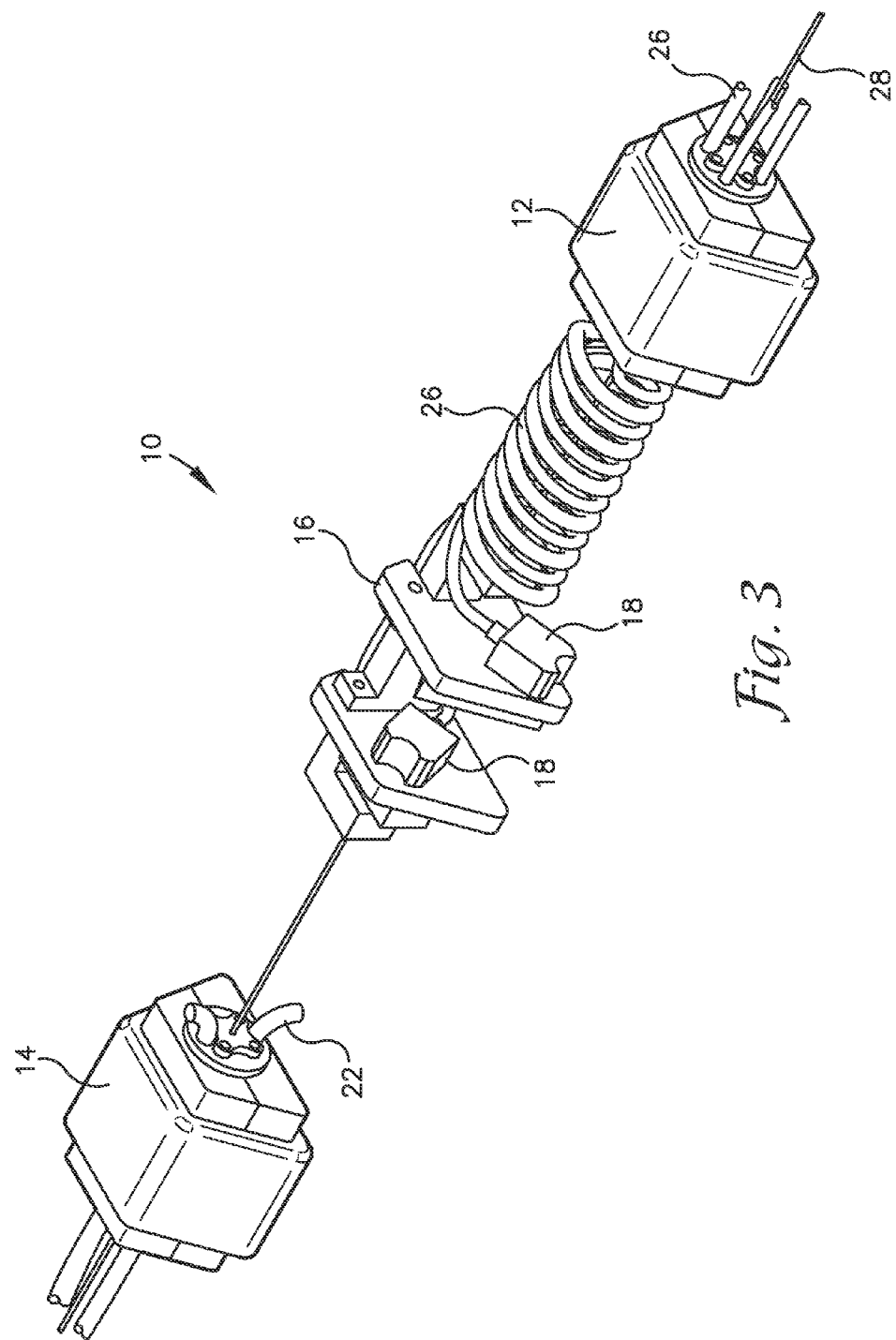
FIG. 3 is a perspective view of an alternative embodiment of the inspection apparatus.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

An inspection apparatus 10 constructed in accordance with embodiments of the present invention is shown in FIGS. 1-7 and generally includes a first plug 12, a second plug 14, and a trolley 16 disposed between the first and second plugs 12,14. The trolley 16 supports or comprises inspection probes 18 for inspecting interior surfaces of a hollow composite part 20, such as the composite stringer illustrated in FIG. 7. The inspection apparatus 10 may be movable to enable short sections of a composite part, such as a stringer, to be filled with liquid, overcoming the disadvantages associated with filling a stringer's full length.

The first and second plugs 12,14 may be sized and shaped to fit within a cavity or hollow tube portion of the composite part 20. For example, the first and second plugs 12,14 may have a substantially trapezoidal shape and may be configured to fit into a hollow composite stringer or a hat-type composite stringer bonded to another composite part to form a hollow tube having a substantially trapezoid-shaped cross-section. However, note that embodiments of the invention may be configured to inspect hollow parts of any material or combination of materials and of any shape and size without departing from the scope of the invention.

In some embodiments of the invention, the first and second plugs 12,14 may have a substantially fixed size and shape. For example, the first and second plugs 12,14 may be slightly oversized blocks of closed-cell foam or may be made from a rigid material incorporating a wiper-type seal (not shown) around its perimeter to form a leak-proof seal between the plugs 12,14 and the interior surfaces of the composite part.

The wiper-type seal may be composed of silicone, rubber, or the like. Alternatively, the first and second plugs 12,14 may be inflatable. For example, for a composite part with an interior having a constant cross-section, the first and second plugs 12,14 may have a substantially fixed size and shape. However, in situations where a single universal inspection apparatus is desired to enable inspection of various diverse part configurations, inflatable embodiments of the first and second plugs 12,14 may be used. Inflatable plugs may be designed to adapt not only to different sizes, but also to different angles and radii.

Figure 4:
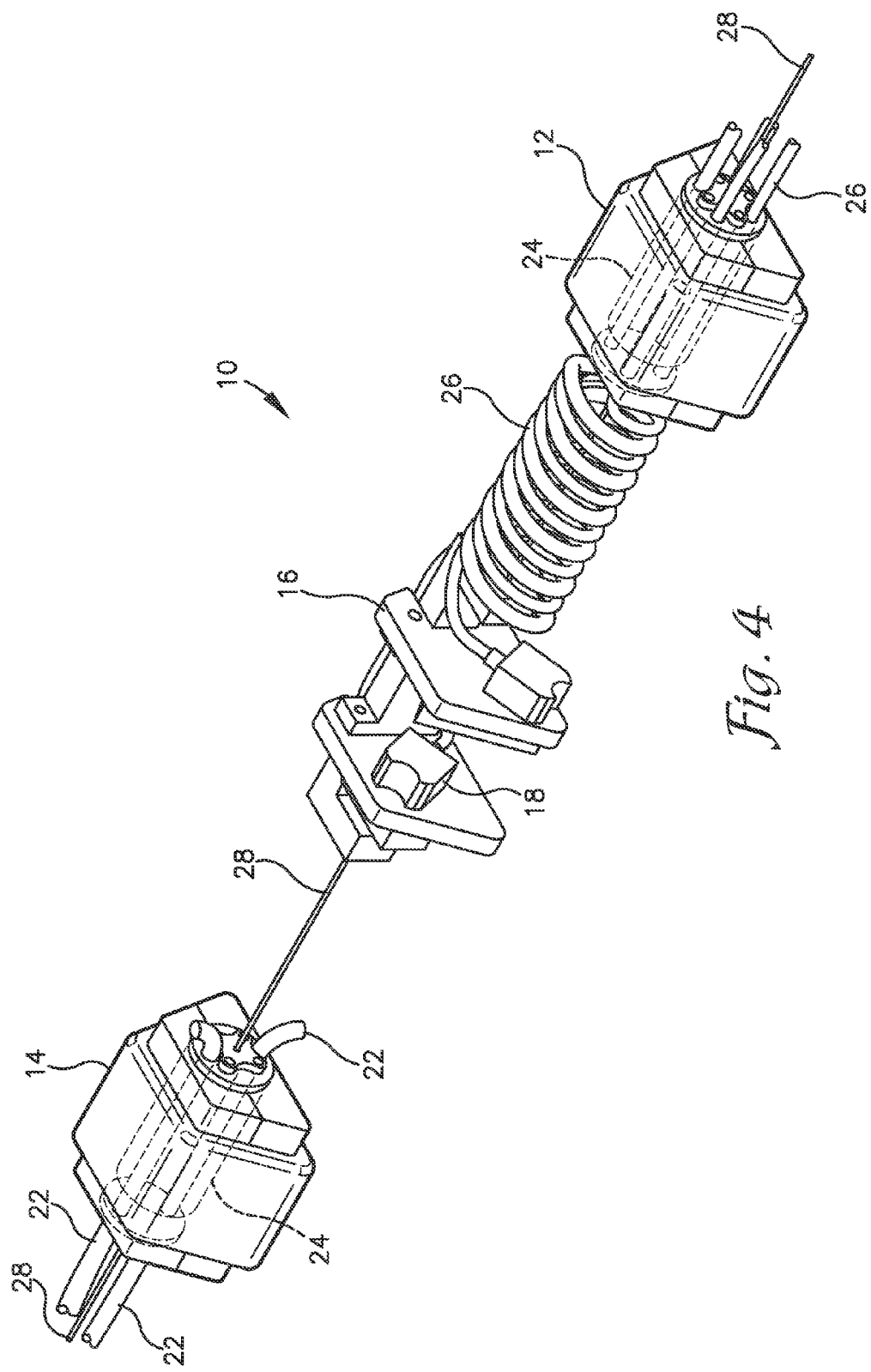
FIG. 4 is a perspective view of the inspection apparatus of FIG. 3, illustrating liquid-carrying tubes and data cables extending through plugs of the inspection apparatus.
Figure 7:
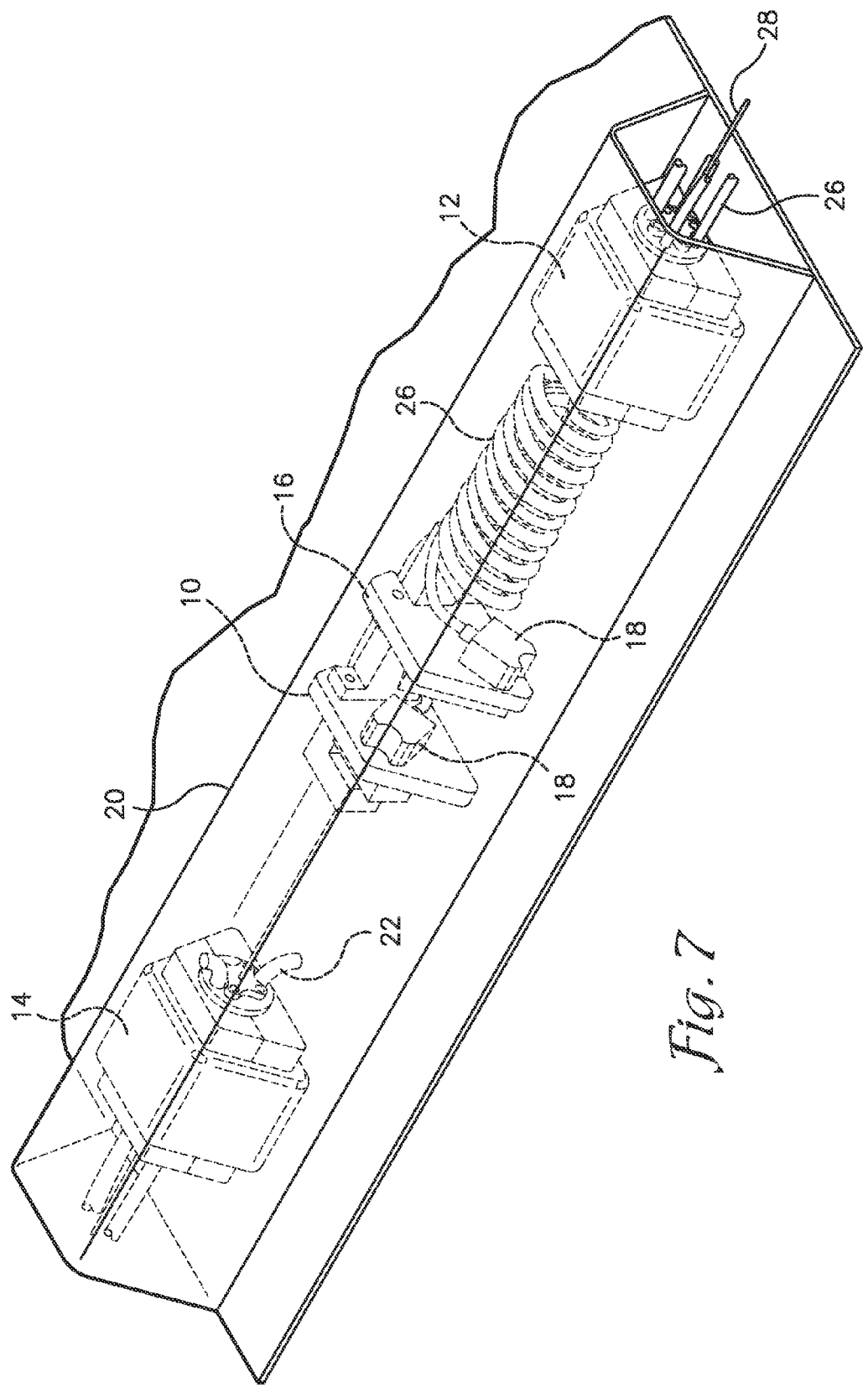
FIG. 7 is a perspective view of a hollow composite part with the inspection apparatus of FIG. 3 located therein for inspection of interior surfaces of the composite part.

At least one of the first and second plugs 12,14 may comprise one or more holes and/or liquid-carrying tubes 22 formed therethrough for delivering fluid between the first and second plugs 12,14, as illustrated in FIGS. 3, 4, and 7. For example, the tubes 22 may be water lines connected to a hole in one of the first and second plugs 12,14 and may transport water or other liquids from a liquid source to a space between the first and second plugs 12,14.

The first and second plugs 12,14 may also each comprise a hole or tube for allowing an air tube (not shown) to run between the first and second plugs for releasing air from an enclosed hollow space within the composite part 20 as the first and second plugs 12,14 are moved therein. For example, if the composite part 20 is sealed at one end, it may be necessary to provide means to exhaust air from inside the composite part 20 as the first and second plugs 12,14 are moved toward the closed end. This may be accomplished by the air tube or tubes extending through both the first and second plugs 12,14 and therefore connecting their exterior sides, providing a flow path for air to be exhausted. Thus, no liquid would flow through the air tube, even when liquid fills the cavity between the first and second plugs 12,14 Furthermore, the first and second plugs 12,14 may have holes formed therein and/or air tight passage tubes 24 passing therethrough for power and/or data cables 26 configured for delivering power and/or data to and from the inspection probes 18 held by the trolley 16.

The trolley 16 may be an apparatus configured to hold one or more of the inspection probes 18, maintaining a desired alignment of and facilitating movement of these inspection probes 18, as illustrated in FIGS. 1, 3 and 4. The inspection probes 18 may be any probes or sensors that require a liquid medium for proper operation. For example, the inspection probes 18 may comprise ultrasound probes, an array of ultrasonic transducers, or any device for emitting frequencies of light or sound waves and receiving reflections from the emitted waves. Note that light waves may include light waves outside of the visible spectrum and sound waves may include sound waves beyond the limits of the audible spectrum. The trolley 16 may have a simple, constant design with a shape substantially matching the interior of a fixed cross-section composite part, or the trolley may have a spring-loaded expanding design (not shown) that maintains the inspection probes 18 at a desired alignment, despite variations in cross-section of the composite part 20.

The trolley 16 may be directly connected and fixed to the first and second plugs 12,14 via some structural supports or may be independently movable between the first and second plugs 12,14. The trolley 16 may be controlled by an elongated actuation element 28 passing through one or both of the first and second plugs 12,14, as later described herein. For example, as in FIG. 1, the trolley 16 may be fixedly attached or integral to the first and second plugs 12,14, and the plugs 12,14 may slide along the interior surfaces of the composite part 20 along with the trolley 16 and the inspection probes 18 as inspection data is being gathered by the inspection probes 18. In cases where the interior surfaces of the composite part 20 are rough or other factors result in high friction between the plugs 12,14 and the composite part 20, independent movement of the trolley 16 with respect to the plugs 12,14 may be desired, as illustrated in FIGS. 3 and 4. For example, the elongated actuation element 28 may slidably pass through the first and/or second plugs 12,14, but remain fixed relative to the trolley 16 such that the trolley 16 can be moved by means of the elongated actuation element 28 while the first and second plugs remain in place within the composite part 20, thus enabling smoother and more precise movement of the trolley 16 and inspection probes 18. In one embodiment of the invention, the elongated actuation element 28 may have stop components 29, as illustrated in FIG. 1, positioned at given travel limit locations thereon, such that the first and second plugs 12,14 may be engaged by the stop components 29 to be pulled or pushed into place within the composite part 20. Therefore, in this embodiment of the invention, actuation of the elongated actuation element 28 may cause the trolley 16 only to travel within the composite part 20 until a limit is reached at which the stop components 29 on the elongated actuation element 28 engage the first and second plugs 12,14, thereby pushing or pulling the plugs 12,14 through the composite part 20. The stop components 29 may be any mechanical stops, bumpers, or other such protrusions extending outward from the elongated actuation element 28.

As noted above, the inspection apparatus 10 may comprise and/or be actuated by the elongated actuation element 28, as illustrated in FIGS. 1-7. The elongated actuation element 28 may be sized and configured to extend a length greater than the distance the first and second plugs 12,14 will traverse to inspect a length of the composite part 20. The elongated actuation element 28 may comprise one or more cables, rods, or tubes configured for moving the trolley 16 and/or the first and second plugs 12,14 through the composite part 20. For example, if the composite part 20 is a stringer accessible at both ends, a cable, as illustrated in FIGS. 3 and 4, may be connected to the trolley 16 and/or the first and second plugs 12,14 and may be pulled, such that the trolley 16 and/or the first and second plugs 12,14 may be positioned at a desired location within the composite part 20. If the composite part 20 is a stringer accessible at only one end, a rod or tube, as illustrated in FIGS. 1, 2, 5, and 6, may be connected to the trolley 16 and/or the first and second plugs 12,14 and may be pushed, such that the trolley 16 and/or the first and second plugs 12,14 may be positioned at a desired location within the composite part 20. Therefore, whether a cable, rod, or tube is to be pushed or pulled to position the trolley 16 and/or the plugs 12,14 may depend on user preference, composite part configuration, and/or the properties of the materials used for the cable or rod (e.g., rigidity, flexibility, etc.).

Figure 5:
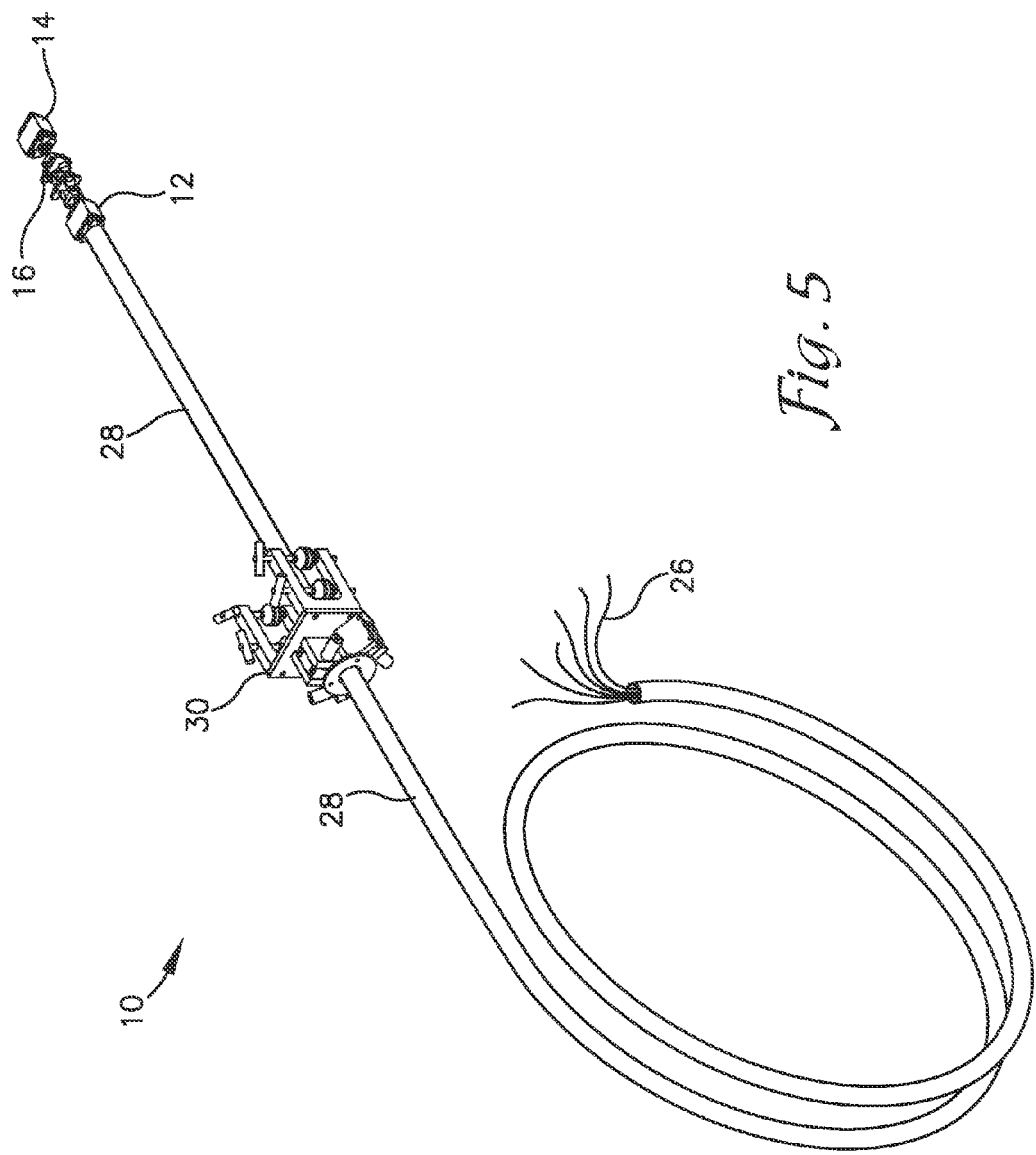
FIG. 5 is a perspective view of another alternative embodiment of the inspection apparatus including a motor configured for actuating movement of the plugs and/or a trolley of the inspection apparatus.
Figure 6:
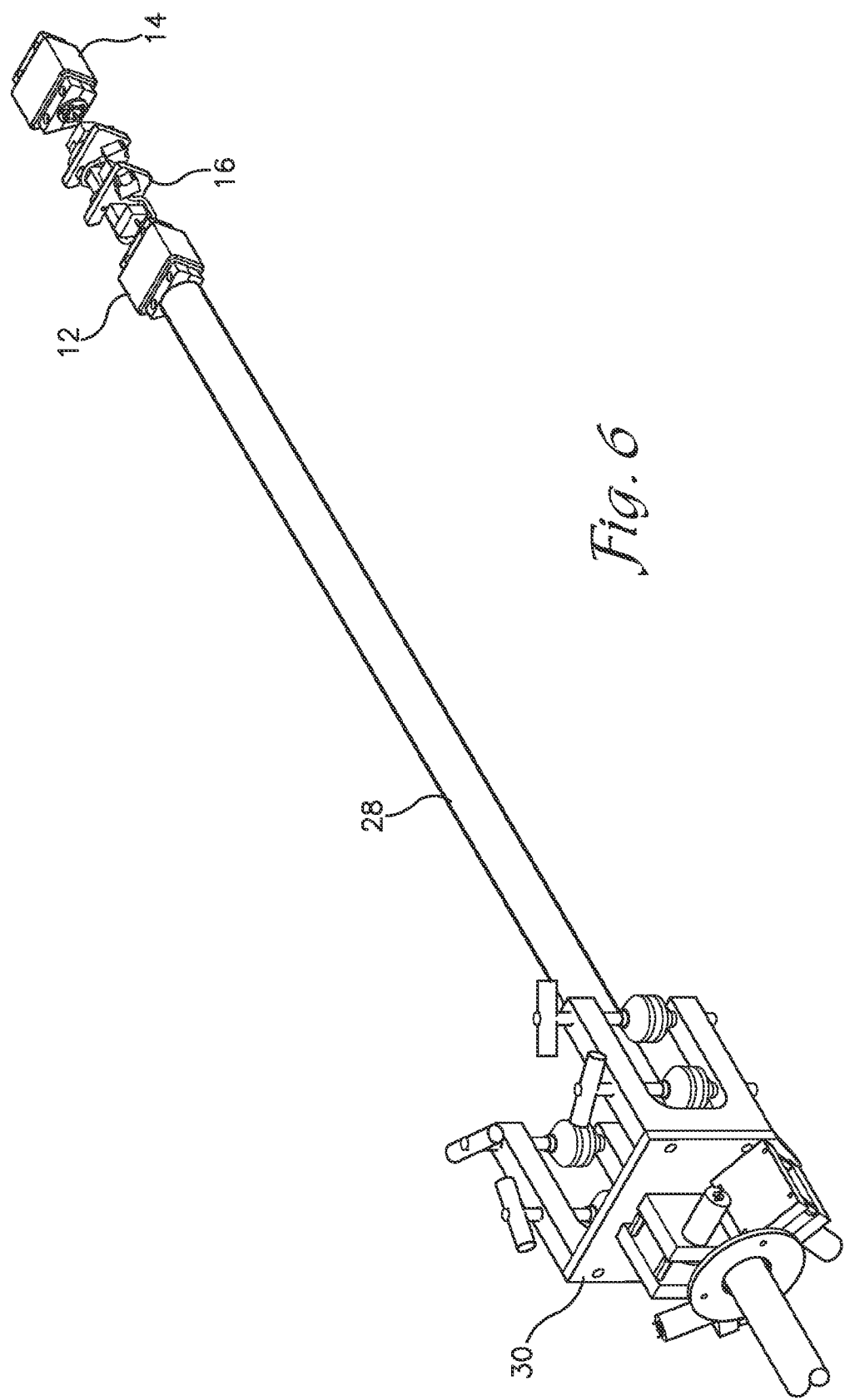
FIG. 6 is a zoomed-in perspective view of the inspection apparatus of FIG. 5.

In some embodiments of the invention, the elongated actuation element 28 may be a tube made of semi-flexible polyethylene material, or some similarly flexible material, as illustrated in FIGS. 5 and 6. The somewhat flexible nature of this tube may help limit moments introduced into the composite part 20 being inspected to prevent damage and may allow coiling of the tube after exiting the part for convenience and a smaller footprint. The tube may also provide a sheath through which power or data cables 26, and/or water lines 22 could be run to protect them and eliminate the potential for snagging. Furthermore, the tube may be fed into and out of the composite part via motors, as illustrated in FIGS. 5 and 6.

Specifically, in some embodiments of the invention, the movement of the trolley 16 and/or the plugs 12,14 may be facilitated by any electrical, mechanical, and/or hydro-mechanical means known in the art. For example, as illustrated in FIGS. 5 and 6, a motor or motors 30 may be used to move the inspection apparatus 10 back and forth through the composite part 20 via actuation of the elongated actuation element 28. Additionally or alternatively, a winch-like system for pulling cable driven embodiments of the invention may be used, or friction drive rollers may be used for pushing and pulling the elongated actuation element 28 in some embodiments of the invention. However, any manual or mechanized methods of pushing or pulling the trolley 16 and/or the first and second plugs 12,14 via the elongated actuation element 28 may be used without departing from the scope of the invention.

In some embodiments of the invention, the inspection apparatus 10 may further comprise an encoder (not shown) configured to provide positional information, such as the position of the inspection apparatus 10 within the composite part, to a non-destructive inspection (NDI) system. For example, the encoder may be mounted externally to the composite part 20 and may sense movement in the elongated actuation element 28 that controls the trolley movement. However, in some cases the elongated actuation element 28, such as a cable, may stretch or other issues may lead to slight inaccuracies. Therefore, in some embodiments of the invention, the encoder may be positioned between the first and second plugs 12,14 to directly sense motion of the trolley 16. This embodiment may also be used in configurations of the invention in which the trolley motion is independently controlled relative to the first and second plugs 12,14. The encoder may be, for example, a magnetic encoder comprising a permanent magnet tape used in conjunction with a Hall Effect sensor chip.

In use, the inspection apparatus 10 may be positioned within the composite part 20, such as within a stringer, or a hat-type stringer bonded to another composite skin. The elongated actuation element 28 may then be pushed or pulled to properly position the inspection apparatus within the composite part 20. For example, the composite part 20 may have some holes intentionally formed therein which would not allow that area of the composite part 20 to be filled with fluid. Therefore, the inspection apparatus 10 may be properly positioned via user knowledge of the areas to be tested and/or using information from the encoder to ensure that the inspection apparatus is properly positioned within the composite part 20.

Then fluid may be fed through the tubes 22 through at least one of the first and second plugs 12,14 and into the space therebetween until the space within the composite part 20 between the plugs 12,14 is completely filled. The fluid may surround the trolley 16 and the inspection probes 18 attached thereto. Then the inspection probes 18 may be used to take desired readings within the composite part 20, as described above. Specifically, the inspection probes 18 may output sound and/or light waves or the like and may then receive reflections resulting from these waves bouncing off of the interior of the composite part 20. Water or other liquids may be a desired medium for certain types of waves utilized by the inspection probes 18, such as ultrasound waves.

In some embodiments of the invention, both the first and second plugs 12,14 and the trolley 16 may move within the composite part 20 to take measurements at various locations. In other embodiments of the invention, the elongated actuation element 28 may be slidable through the first and/or second plugs 12,14 such that the trolley 16 may move via actuation of the elongated actuation element 28 back and forth between the first and second plugs 12,14.

Once the inspection is completed, the fluid may be drained via the holes or tubes 22 through which the liquid was delivered between the first and second plugs 12,14. For example, valves fluidly coupled with the holes or the tubes 22 maybe opened to allow liquid to drain out from between the first and second plugs 12,14. Then the elongated actuation element 28, such as a cable, rod, or tube, may be actuated to push or pull the inspection apparatus 10 to remove the inspection apparatus 10 from the composite part 20.

Although the invention has been described with reference to the preferred embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An inspection apparatus comprising:
   a first plug configured for fitting within a hollow composite part and forming a leak-proof seal against an interior surface of the hollow composite part;
   a second plug configured for fitting within the hollow composite part, forming a leak-proof seal against the interior surface of the hollow composite part, and spaced a distance apart from the first plug;
   a trolley configured to be positioned between the first plug and the second plug, independently moveable relative to the first and second plugs in a direction toward and away from the first and second plugs, and configured to support at least one inspection probe for testing an interior of a composite part; and
   a cable, rod, or tube fixed relative to the trolley and fixed to or extending through at least one of the first and second plugs, wherein the cable, rod, or tube is configured to pull or push at least one of the trolley and the first and second plugs within the composite part.

2. The apparatus of claim 1, further comprising one or more tubes extending through at least one of the first and second plugs and configured to supply a liquid to the space between the first and second plugs within the composite part.

3. The apparatus of claim 1, wherein the first and second plugs are made of closed-cell foam and are sized and shaped slightly larger than the interior of the composite part.

4. The apparatus of claim 1, wherein the first and second plugs each comprise a rigid material with a wiper-type seal around a periphery thereof, forming the leak-proof seal.

5. The apparatus of claim 1, further comprising the at least one inspection probe and at least one of a power cable and a data cable extending from the inspection probe through at least one of the plugs and configured to provide at least one of power to the inspection probe and data from the inspection probe to a non-destructive inspection (NDI) system or computer to be analyzed thereby.

6. The apparatus of claim 5, wherein at least one of the power cable and the data cable extend through a tube configured to connect with and actuate at least one of the first plug, the second plug, and the trolley through the composite part.

7. The apparatus of claim 1, further comprising an actuation apparatus for pushing or pulling the cable, rod, or tube.

8. The apparatus of claim 7, wherein the actuation apparatus is a motor configured for actuating the pushing and pulling of the cable, rod, or tube.

9. An inspection apparatus comprising:
   a first plug configured for fitting within a hollow composite part and forming a leak-proof seal against an interior surface of the hollow composite part;
   a second plug configured for fitting within the hollow composite part, forming a leak-proof seal against the interior surface of the hollow composite part, and spaced a fixed distance apart from the first plug;
   a trolley configured to be positioned between the first plug and the second plug, moveable relative to the first and second plugs in a direction toward and away from the first and second plugs, and configured to support at least one inspection probe for testing an interior of a composite part; and
   an elongated actuation element extending through the first plug, the second plug, and the trolley and fixed relative to the trolley, wherein the elongated actuation element is slidable through the first and second plugs, wherein the elongated actuation element is configured to pull or push the trolley within the composite part and between the first and second plugs.

10. The apparatus of claim 9, wherein the elongated actuation element is a cable, rod, or tube.

11. The apparatus of claim 9, further comprising one or more tubes extending through at least one of the first and second plugs and configured to supply a liquid to the space between the first and second plugs when positioned within the composite part.

12. The apparatus of claim 9, wherein the first and second plugs are made of closed-cell foam and are sized and shaped slightly larger than the interior of the composite part.

13. The apparatus of claim 9, wherein the first and second plugs each comprise a rigid material with a wiper-type seal around a periphery thereof, forming the leak-proof seal.

14. The apparatus of claim 9, further comprising the at least one inspection probe and at least one of a power cable and a data cable extending from the inspection probe through at least one of the plugs and configured to provide at least one of power to the inspection probe and data from the inspection probe to a non-destructive inspection (NDI) system or computer to be analyzed thereby.

15. The apparatus of claim 14, wherein at least one of the power cable and the data cable extend through the elongated actuation element.

16. The apparatus of claim 9, further comprising a motorized apparatus for pushing or pulling the cable, rod, or tube.

17. A method for inspecting an interior surface of a hollow composite part having at least one opening through which an inspection apparatus can be inserted, the method comprising:
   inserting the inspection apparatus through the opening of the hollow composite part, wherein the inspection apparatus comprises:
   a first plug configured for forming a leak-proof seal against the interior surface of the hollow composite part;
   a second plug configured for forming a leak-proof seal against the interior surface of the hollow composite part and spaced a distance apart from the first plug;
   a trolley positioned between the first plug and the second plug, slidable back and forth between the first and second plugs; and
   at least one inspection probe supported by the trolley and configured for testing the interior surface of the composite part;
   pushing or pulling an elongated actuation element attached to the inspection apparatus, moving the inspection apparatus to a desired area to be inspected within the composite part ;
   filling a space between first and second plugs with a liquid, such that liquid is trapped between the first and second plugs and surrounds the trolley and the at least one inspection probe; and
   inspecting the interior surface of the hollow composite part with the at least one inspection probe.

18. The method of claim 17, wherein the at least one inspection probe transmits sound waves and receives reflections of said sound waves.

19. The method of claim 17, further comprising the steps of:
wherein the elongated actuation element is slidable through at least one of the first and second plugs and further comprises at least one stop component configured to engage with at least one of the first and second plugs when the elongated actuation element is pushed or pulled a particular travel limit distance,
wherein the method further comprises pushing or pulling the elongated actuation element beyond the particular travel limit distance such that the at least one stop component engages the at least one of the first and second plugs, thereby pushing or pulling the at least one of the first and second plugs through the composite part.

20. An inspection apparatus comprising:
a first plug configured for fitting within a hollow composite part and forming a leak-proof seal against an interior surface of the hollow composite part;
a second plug configured for fitting within the hollow composite part, forming a leak-proof seal against the interior surface of the hollow composite part, and spaced a distance apart from the first plug;
a trolley configured to be positioned between the first plug and the second plug, independently moveable relative to the first and second plugs in a direction toward and away from the first and second plugs, and configured to support at least one inspection probe for testing an interior of a composite part; and
one or more tubes extending through at least one of the first and second plugs and configured to supply a liquid to the space between the first and second plugs within the composite part.

21. The apparatus of claim 20, wherein the first and second plugs are made of closed-cell foam and are sized and shaped slightly larger than the interior of the composite part.

22. The apparatus of claim 20, wherein the first and second plugs each comprise a rigid material with a wiper-type seal around a periphery thereof, forming the leak-proof seal.

23. An inspection apparatus comprising:
a first plug configured for fitting within a hollow composite part and forming a leak-proof seal against an interior surface of the hollow composite part;
a second plug configured for fitting within the hollow composite part, forming a leak-proof seal against the interior surface of the hollow composite part, and spaced a distance apart from the first plug;
at least one inspection probe;
a trolley configured to be positioned between the first plug and the second plug, independently moveable relative to the first and second plugs in a direction toward and away from the first and second plugs, and configured to support the at least one inspection probe for testing an interior of a composite part; and
at least one of a power cable and a data cable extending from the inspection probe through at least one of the plugs and configured to provide at least one of power to the inspection probe and data from the inspection probe to a non-destructive inspection (NDI) system or computer to be analyzed thereby.

24. The apparatus of claim 23, wherein at least one of the power cable and the data cable extend through a tube configured to connect with and actuate at least one of the first plug, the second plug, and the trolley through the composite part.

25. The apparatus of claim 23, wherein the first and second plugs are made of closed-cell foam and are sized and shaped slightly larger than the interior of the composite part.

26. The apparatus of claim 23, wherein the first and second plugs each comprise a rigid material with a wiper-type seal around a periphery thereof, forming the leak-proof seal.

* * * * *